United States Patent [19]

Monoe et al.

[11] Patent Number: 6,133,471
[45] Date of Patent: Oct. 17, 2000

[54] PROCESS FOR PRODUCING CHROMANS

[75] Inventors: Hiroyuki Monoe; Junko Sato, both of Kitakanbara-gun, Japan; Koichi Kanehira, New York, N.Y.; Yoshin Tamai, Kitakanbara-gun, Japan

[73] Assignee: KURARAY Co., Ltd., Kurashiki, Japan

[21] Appl. No.: 09/427,117

[22] Filed: Oct. 26, 1999

Related U.S. Application Data

[62] Division of application No. 09/118,318, Jul. 17, 1998.

[30] Foreign Application Priority Data

Jul. 17, 1997 [JP] Japan ................................. 9-207362

[51] Int. Cl.$^7$ .......................... C07C 43/115; C07C 69/84
[52] U.S. Cl. .......................... 560/104; 560/106; 560/130; 568/662; 568/664
[58] Field of Search .................................... 560/104, 106, 560/130; 568/662, 664

[56] References Cited

U.S. PATENT DOCUMENTS 4,692,555  9/1987  Shin .
5,004,758  4/1991  Boehm et al. .
5,495,026  2/1996  Fukumoto et al. .

FOREIGN PATENT DOCUMENTS 60-92283  5/1985  Japan .

OTHER PUBLICATIONS

"Daiyukikagaku", vol. 14, pp. 215–220, 1959.

Tsutomu Inoue, et al., Bull. Chem. Soc. Japan, vol. 63, No. 4, pp. 1062 to 1067, "A New Synthesis of O–Quinonemethides and Their Inter–and Inrramolecular Cyclization Reactions", 1990.

Kostas Karabelas, et al., J. Am. Chem. Soc., vol. 112, pp. 5372–5373, "(Trimethylsilyl)Methyl)–1,4–Benzoquinones, Generation and Trapping of O–Quinone Methides", Feb. 20, 1990.

*Primary Examiner*—Joseph K. McKane
*Assistant Examiner*—Taofiq A. Solola
*Attorney, Agent, or Firm*—Oblon, Spivak, McClelland, Maier & Neustadt, P.C.

[57] ABSTRACT

A process for producing chromans, comprising reacting a phenol, a formaldehyde and an alcohol in the presence of a secondary amine and an acid, to generate an alkoxymethylphenol compound with the ortho position to the phenolic hydroxyl group substituted with an alkoxymethyl group, and reacting the alkoxymethylphenol compound with an unsaturated compound having a carbon-carbon double bond.

1 Claim, No Drawings

PROCESS FOR PRODUCING CHROMANS

This is a Division of application Ser. No. 09/118,318 filed Jul. 17, 1998, now allowed.

BACKGROUND OF THE INVENTION

1. Field of the Invention

The present invention relates to a process for producing chromans, a process for producing intermediate products useful for the synthesis of chromans, and a novel intermediate product useful for the synthesis of chromans.

The chromans produced in accordance with the present invention, including, for example, 2,5,7,8-tetramethyl-6-acetoxy-2-(4-nitrophenyloxy)methylchroman, are useful as intermediate products for biologically active substances, such as tocopherols, and pharmaceutical agents, such as therapeutic agents of diabetes mellitus, or as intermediate products for polymer materials, such as engineering resins, and, additionally, as stabilizers of organic substances, such as fats and fatty oils and synthetic resins.

2. Discussion of the Background

Conventional processes for producing chromans (a) to (d), described below, are known.

(a) Ring Closing Reaction of an Allyl Phenol

A process for producing chromans by ring closing of an allyl phenol obtained by reacting an allyl halide, an allyl alcohol or a diolefin with a phenol (see "DAIYUKIKAGAKU", Vol. 14, pages 215–217).

According to the conventional process (a), for example, a case wherein sodium phenolate is used as a phenol and 1,1-dimethyl-3-halogenated-1-propene is used as an allyl halide is illustrated as follows:

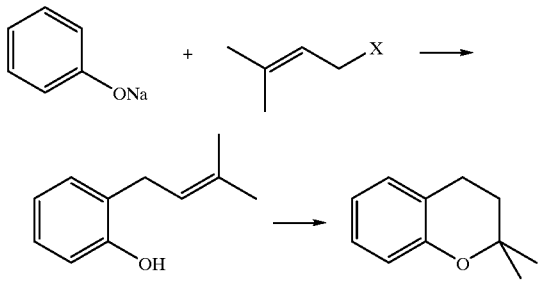

where X represents a halogen atom.

(b) Reaction of o-oxybenzyl Alcohol with an Unsaturated Compound

A process for producing chromans by heating and reacting together o-oxybenzyl alcohol and an unsaturated compound with no solvent at a temperature within a range of 180 to 220° C. (see "DAIYUKIKAGAKU", Vol.14, page 220).

According to conventional process (b), for example, a case wherein 1-propene is used as an unsaturated compound is illustrated as follows:

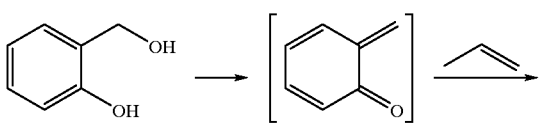

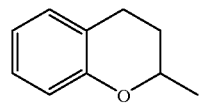

(c) Reaction of the Oxidized Product of o-[1-(alkylthio) alkyl]phenol with an Unsaturated compound.

A process for producing chromans by oxidizing o-[1-(alkylthio)alkyl]phenol with silver oxide under mild conditions, and reacting the resulting oxidized product with a vinyl ether [see Bull. Chem. Soc. Japan, Vol. 63, page 1062 (1990)].

According to the conventional process (c), a case wherein vinyl methyl ether is used as a vinyl ether is illustrated as follows:

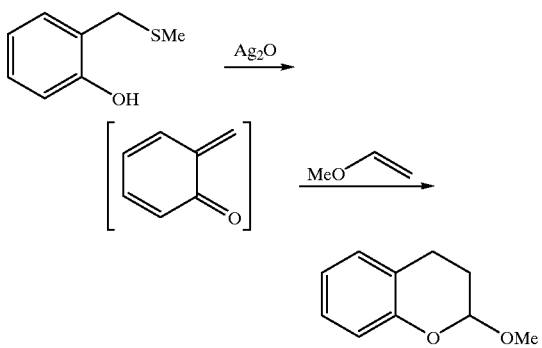

(d) Reaction of a Phenol, a Formaldehyde and an Unsaturated Compound

A process for producing chromans by heating and reacting a phenol, a formaldehyde and an unsaturated compound in a solvent of a hydrocarbon or a halogenated aromatic compound at a temperature within a range of 160 to 250° C. (see Japanese Patent Application Laid-open 92283/1985).

According to tile conventional process (d), a case wherein a pyrroline based compound is used as an unsaturated compound is illustrated as follows:

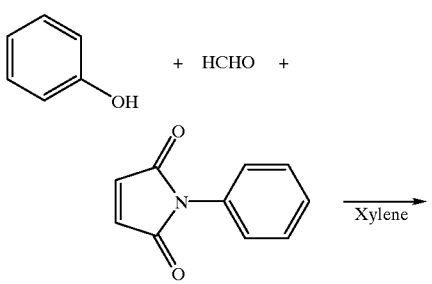

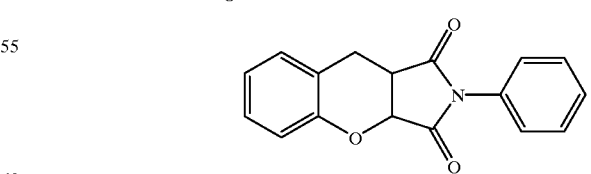

However, the aforementioned conventional processes (a) to (d) have the following problems, and, therefore, these processes are not satisfactory for producing chromans.

According to conventional process (a), the desired chroman sometimes cannot be produced, depending on the types of the substituents present on the allyl compound or the diolefin which is reacted with the phenol, and the yield is generally low. According to conventional process (b), it is difficult to synthesize the o-oxybenzyl alcohol as the starting material in a high yield, and, therefore, it is difficult to produce chromans in high yield. According to conventional process (c), it is required to use a specific compound o-[1-(alkylthio)alkyl] phenol as the starting material. To oxidize the phenol, it is also required to use expensive silver oxide at the large amount of an equimolar amount or more, and, therefore, the production cost of the desired chromans is increased, disadvantageously. According to conventional process (d), the yield of chromans is generally as low as 10 to 50%.

An object in the field of chroman synthesis is to provide a process for producing chromans, by using readily available starting materials and inexpensive starting materials, in a high yield in a simple and smooth manner at an industrially high productivity. It is another object in the field of chroman synthesis to provide compounds to be used as intermediates for producing chromans.

The present inventors have made efforts to attain these objects. The inventors have found that chromans can be produced in a simple fashion in high yield, by using a readily available phenol compound, a formaldehyde and an unsaturated compound having a carbon-carbon double bond as starting materials and reacting them in the presence of a secondary amine and an acid (see U.S. Pat. No. 5,495,926).

According to this process, the desired chromans can be produced as follows. In the following reaction formulas, herein, an example is illustrated wherein 4-acetoxy-2,3,5-trimethylphenol is used as the phenol compound; 2-methyl-2-propen-1-ol is used as the unsaturated compound having a carbon-carbon double bond; and dibutylamine is used as the secondary amine; and acetic acid is used as the acid:

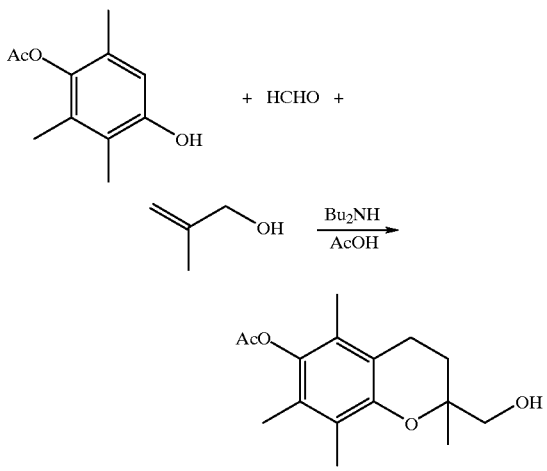

Compared with the aforementioned conventional processes (a) to (d), the process of the present inventors is excellent in that the desired chromans can be produced industrially in a simple manner at low cost, in a high yield, by using readily available starting materials, particularly in that the chromans can be produced in an extremely high yield, when using a compound having a carbon-carbon double bond and a hydroxyl group within the molecule or a compound having a carbon-carbon double bond and an electron withdrawing group such as ester group and acyl group, which is directly bonded to a carbon atom composing the carbon-carbon double bond thereof.

SUMMARY OF THE INVENTION

After further investigations the present inventors have now found that chromans can be produced in a high yield by reacting a phenol compound, a formaldehyde and an alcohol in the presence of a secondary amine and an acid at a specific temperature to generate an alkoxymethylphenol compound, removing the secondary amine out of the reaction system (step 1), and then reacting the resulting alkoxymethylphenol compound with a specific compound having a carbon-carbon double bond (step 2); and that the desired chromans can be produced in a smooth manner in a high yield at such two-step process, particularly when using a compound having a carbon-carbon double bond and no hydroxyl groups within the molecule and no electron withdrawing groups directly bonded to a carbon atom composing the carbon-carbon double bond thereof.

Furthermore, the present inventors have found that specific alkoxymethylphenol compounds obtained in step 1 according to the process for producing chromans at the two-step reaction process are novel compounds, which can be effectively utilized as intermediate products for producing chromans and the like, and based on these findings, the present invention has been accomplished.

Accordingly, the present invention provides a process for producing chromans, comprising:

Step 1: comprising reacting a phenol compound having at least one of the ortho positions to the phenolic hydroxyl group being unsubstituted, a formaldehyde and an alcohol in the presence of a secondary amine and an acid at a temperature within a range of 50 to 130° C., to produce an alkoxymethylphenol compound with the ortho position to the phenolic hydroxyl group being substituted with an alkoxymethyl group, and then removing the secondary amine from the reaction mixture; and Step 2: comprising reacting the alkoxymethylphenol compound obtained in step 1 with a compound having a carbon-carbon double bond and no hydroxyl group within the molecule and no electron withdrawing group directly bonded to a carbon atom composing the carbon-carbon double bond thereof, at a temperature of 150° C. or more, to produce the chroman.

Additionally, the present invention includes a process for producing chromans, comprising reacting an alkoxymethylphenol compound with the ortho position to the phenolic hydroxyl group being substituted with an alkoxymethyl group with a compound having a carbon-carbon double bond and no hydroxyl group within the molecule and no electron withdrawing group directly bonded to a carbon atom composing the carbon-carbon double bond thereof at a temperature of 150° C. or more.

Also, the present invention includes a process for producing an alkoxymethylphenol compound with the ortho positions to the phenolic hydroxyl group being substituted with an alkoxymethyl group, comprising reacting a phenol compound having at least one of the ortho positions to the phenolic hydroxyl group being unsubstituted, a formaldehyde and an alcohol in the presence of a secondary amine and an acid at a temperature within a range of 50 to 130° C.

In addition, the present invention includes the alkoxymethylphenol compound represented by the following general formula (2):

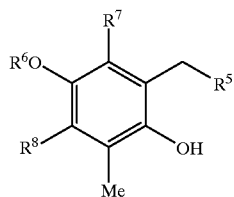

(2)

where $R^5$ represents an alkoxyl group; $R^6$ represents an aliphatic acyl group, an aromatic acyl group, benzyl group or a hydrogen atom; and $R^7$ and $R^8$ each independently represent a hydrogen atom or methyl group.

A more complete appreciation of the invention and many of the attendant advantages thereof will be readily obtained as the same becomes better understood by reference to the following detailed description.

DETAILED DESCRIPTION OF THE INVENTION

In step 1 of the present invention, a phenol compound is used which has at least one of the ortho positions to the phenolic hydroxyl group unsubstituted.

In step 1, the reaction proceeds following the reaction scheme shown below, to produce an alkoxymethylphenol compound represented by the general formula (3) as an intermediate product:

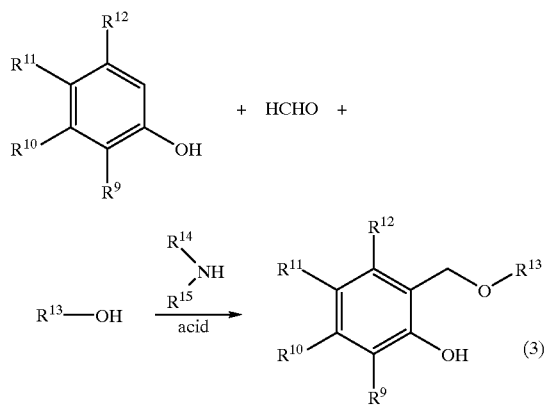

(3)

wherein $R^9$, $R^{10}$, $R^{11}$ and $R^{12}$ each independently represent a hydrogen atom; monovalent hydrocarbon groups, which may be substituted, such as an alkyl group, an aryl group and an aralkyl group; monovalent hydrocarboxy groups such as an aliphatic acyloxy group, an aromatic acyloxy group, an alkoxyl group, phenoxy group, and benzyloxy group; or two or three or more of $R^9$, $R^{10}$, $R^{11}$ and $R^{12}$ together may form a closed ring together with the carbon atom of the benzene ring to which these groups are bonded; and $R^{13}$ represents alcohol residues, representing for example a linear, branched or cyclic alkyl group or monovalent hydrocarbon groups with aromatic rings such as benzyl group and phenethyl group; $R^{14}$ and $R^{15}$ each independently represent an alkyl group, an aryl group and an aralkyl group; or $R^{14}$ together with $R^{15}$ represents a hydrocarbon group which may form a ring together with the nitrogen atom of a secondary amine.

The phenol compounds to be used as the starting material in step 1 of the present invention include phenol, cresol, hydroquinone, naphthol, phenanthrol, alkoxyphenol (for example, methoxyphenol, ethoxyphenol), nitrophenol, acyloxyphenol (for example, 4-acetoxyphenol), 2-alkyl-4-acyloxyphenol (for example, 2-methyl-4-acetoxyphenol), 2,3-dialkyl-4-acyloxyphenol (for example, 2,3-dimethyl-4-acetoxyphenol), 4-acyloxy-3,5-dialkylphenol (for example, 4-acetoxy-3,5-dimethylphenol), 4-acyloxy-2,3,5-trialkylphenol (for example, 4-acetoxy-2,3,5-trimethylphenol), 2-alkyl-4-benzyloxyphenol (for example, 2-methyl-4-benzyloxyphenol), 2,3-dialkyl-4-benzyloxyphenol (for example, 2,3-dimetlyl-4-benzyloxyphenol), 4-benzyloxy-3,5-dialkylphenol (for example, 4-benzyloxy-3,5-dimethylphenol), 4-benzyloxy-2,3,5-trialkylphenol (for example, 4-benzyloxy-2,3,5-trimethylphenol), 2-alkylhydroquinone (for example, 2-methylhydroquinone), 2,3-dialkylhydroquinone (for example, 2,3-dimethylhydroquinone), 3,5-dialkylhydroquipone (for example, 3,5-dimethylhydroquinone), 2,3,5-trialkylhydroquinone (for example, 2,3,5-trimethylhydroquinone), and the like.

In the present invention, particularly when using a phenol compound represented by the following general formula (4) as the phenol compound:

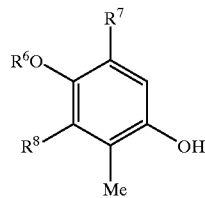

(4)

wherein $R^6$ represents an aliphatic acyl group, an aromatic acyl group, benzyl group or a hydrogen atom; $R^7$ and $R^8$ each independently represent a hydrogen atom or methyl group, an alkoxymethylphenol compound represented by the following general formula (2), which is a novel compound, is produced:

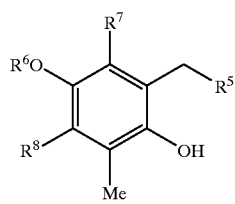

(2)

wherein $R^5$ represents an alkoxyl group; and $R^6$, $R^7$ and $R^8$ represent the same groups as those described above.

In the phenol compound represented by the general formula (4) and the alkoxymethylphenol compound represented by the general formula (2), specific examples of an aliphatic acyl group of $R^6$ include a formyl group, acetyl group, propionyl group, butyryl group, valeryl group and the like, which are derived from linear or branched lower aliphatic carboxylic acids; specific examples of an aromatic acyl group of $R^6$ include a benzoyl group, toluoyl group, xyloyl group and the like, which are derived from aromatic carboxylic acids.

The alkoxyl group $R^5$ in the alkoxymethylphenol compound represented by the general formula (2) corresponds to the group —O—$R^{13}$ in the alkoxymethylphenol compound represented by the general formula (3), which is the alkoxyl group derived from alcohol ($R^{13}$—OH) to be used for producing the alkoxymethylphenol compound represented by the general formula (3) or the general formula (2). Specific examples of the alcohol ($R^{13}$—OH) are as described below, and $R^5$ and —O—$R^{13}$ are preferably a primary alkoxyl group or a secondary alkoxyl group.

The novel alkoxymethylphenol compound represented by the general formula (2) can effectively be utilized for producing chromans, like other alkoxymethylphenol compounds contained within the category of the alkoxymethylphenol compound represented by the general formula (3), and thus, the present invention contains the process for producing the alkoxymethylphenol compound represented by the general formula (3) (the production process corresponding to step 1) and the novel alkoxymethylphenol compound represented by the general formula (2) which is obtainable by the process, within the scope of the present invention.

In step 1 for producing alkoxymethylphenol compounds of the present invention, examples of the formaldehyde include formalin, formalin based linear polymers such as paraformaldehyde and cyclic acetal oligomers such as trioxane and tetraoxane, and one or two or more of them may be used, i.e., compounds that produce formaldehyde in the reaction solution:

In step 1 for producing alkoxymethylphenol compounds of the present invention, a primary alcohol and/or secondary alcohol may preferably be used as the alcohol, in respect of reactivity and selectivity. Specific examples thereof include saturated aliphatic primary alcohols such as methanol, ethanol, 1-propanol, 1-butanol, 1-hexanol, 1-octanol and 2-ethyl- 1-hexanol; saturated aliphatic secondary alcohols such as 2-propanol, 2-butanol and cyclohexanol; saturated aliphatic diols such as ethylene glycol, propylene glycol, 1,4-butanediol and hexanediol; alcohols with aromatic rings, such as benzyl alcohol and phenethyl alcohol. In the present invention, one or two or more of the alcohols may be used.

The alkoxyl group —O—$R^{13}$ in the alkoxymethylphenol compound represented by the general formula (3) and alkoxyl group $R^5$ in the alkoxymethylphenol compound represented by the general formula (2) are derived from the alcohol described above.

In the present invention, the step 1, namely the reaction of a phenol compound, a formaldehyde and an alcohol, is conducted in the presence of a secondary amine and an acid. The secondary amine and the acid act as catalysts and/or reaction promoting agents for generating alkoxymethylphenol compounds.

As the secondary amine, any of the aliphatic secondary amines and/or aromatic secondary amines may be used, with no specific limitation. Specific examples thereof include linear aliphatic secondary amines such as diethylamine, dibutylamine and dioctylamine; cyclic secondary amines such as piperidine, pyrrolidine and morpholine; and the like may be used. In the present invention, one or two or more of the secondary amines described above may be used.

As the acid, any of the organic acids and/or inorganic acids may be used, and in respect of selectivity, organic acids are preferably used, and more preferably, a saturated aliphatic carboxylic acid and/or aromatic carboxylic acid having 2 to 8 carbon atoms are used. Specific examples thereof include acetic acid, propionic acid, butyric acid, 2-methylpropionic acid, valeric acid, 3-methylbutanoic acid, 2-methylbutanoic acid, hexanoic acid, heptanoic acid, octanoic acid and benzoic acid; and the like. In the present invention, one or two or more of these acids described above may be used.

So as to promote the generation of alkoxymethylphenol compounds smoothly in step 1 of the present invention, the amount of formaldehyde is used preferably within the range of 0.8 to 10 molar equivalents, more preferably within the range of 1 to 2 molar equivalents, while the amount of alcohol is used preferably within the range of 0.8 to 20 molar equivalents, more preferably within the range of 1 to 10 molar equivalents based on one molar equivalent of the phenol compound. The ranges of molar equivalent for the formaldehyde include all specific values and subranges therebetween, including 0.9, 1.5, 2, 3, 4, 5 and 8 molar equivalents. The ranges of molar equivalent for the alcohol include all specific values and subranges therebetween, including, where appropriate, 0.9, 1.5, 2, 3, 4, 5, 8, 12, 15 and 18 molar equivalents.

So as to promote the generation of alkoxymethylphenol compounds smoothly in step 1 of the present invention, the amount of secondary amine is used preferably within the range of 0.001 to 1.0 molar equivalent, more preferably within the range of 0.01 to 0.5 molar equivalents, while the amount of acid is used preferably within the range of 0.01 to 5 molar equivalents, more preferably within the range of 0.1 to 1.0 molar equivalent based on one molar equivalent of the phenol compound. The ranges of molar equivalent for the amine include all specific values and subranges therebetween, such as 0.002, 0.005, 0.008, 0.02, 0.05, 0.08, 0.1, 0.2, 0.3 and 0.4 molar equivalents. The ranges of molar equivalent for the acid include all specific values and subranges therebetween, including 0.02, 0.05, 0.08, 0.2, 0.3, 0.5, 1, 2.5, 3 and 4 molar equivalents.

In the step 1 of the present invention, the reaction can be conducted without solvent or in the presence of solvent. When solvent is used, inert solvents such as toluene, xylene, and N-methylpyrrolidone may be used, and the amount of the solvent is preferably within the range of 50 to 1,000 parts by weight based on 100 parts by weight of the phenol compound, inclusive of all specific values and subranges therebetween (e.g., 100, 200, 250, 300, 500, 600 and 750 parts by weight based on 100 parts by weight of the phenol compound).

In the step 1 of the present invention, the reaction is conducted by mixing together given amounts of a phenol compound, a formaldehyde, an alcohol, a secondary amine and an acid, and heating the resulting mixture at a temperature within the range of 50 to 130° C., preferably within the range of 80 to 120° C., in the presence of solvent if necessary. These temperature ranges include of all specific values and subranges therebetween including 60, 70, 75, 85, 90, 100, 1 10, 115 and 125° C. When the boiling point of an alcohol to be used is lower than the aforementioned reaction temperature, the reaction is preferably promoted under pressurizing conditions. The reaction time may be varied, depending on the types of the phenol compound, formaldehyde and the alcohol to be used, the ratio thereof to be used and the reaction temperature, but generally, the reaction time is preferably adopted within the range of 30 minutes to 24 hours, inclusive of all specific values and subranges therebetween including 1, 2, 5, 10, 12, 15 and 20 hour reaction times.

The secondary amine used in step 1 is required to be removed out of the reaction system, so as to obtain the desired chromans in a smooth manner in the subsequent step 2. Then, the removal of the secondary amine from the reaction system in step 1 may be conducted by extracting the secondary amine by adding solvent such as aromatic hydrocarbons such as toluene and xylene; and ethers such as diisopropyl ether to the reaction system, or using a distillation process under reduced pressure, and the like. Thus, at least a portion of the secondary amine remaining in the reaction mixture is removed after production of the alkoxymethylphenol compound. The amount of amine removed should be sufficient such that the chroman is produced in step 2 of the process. The alkoxymethylphenol compound generated in step 1 can be further subject to a washing process and the like, then isolated, and the resulting isolated compound can be subjected to step 2.

In step 2, the alkoxymethylphenol compound obtained in step 1 reacts with a specific unsaturated compound having a carbon-carbon double bond, to produce the desired chromans.

In step 2, the unsaturated compound for the reaction with the alkoxymethylphenol compound is a compound having a carbon-carbon double bond and no hydroxyl group within the molecule and no electron withdrawing group directly bonded to a carbon atom composing the carbon-carbon double bond.

Among them, in the present invention, a compound having a carbon-carbon double bond as represented by the following general formula (1) (hereafter abbreviated as unsaturated compound (1)) may preferably be used:

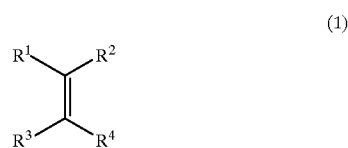

wherein $R^1$, $R^2$, $R^3$ and $R^4$ each independently represent a hydrogen atom, an alkyl group, an aryl group or an alkyl group or aryl group substituted with the proviso that non-protected hydroxyl groups and non-protected amino groups are excluded as substituents.

In step 2 of the present invention, the reaction of the unsaturated compound (1) with the alkoxymethylphenol compound obtained in step 1 represented by the general formula (3) proceeds following the reaction formula shown below, to generate chromans represented by the general formula (5).

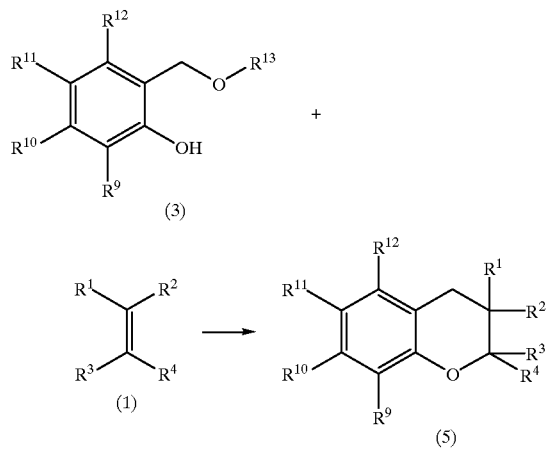

In the formula, $R^1$, $R^2$, $R^3$, $R^4$, $R^9$, $R^{10}$, $R^{11}$, $R^{12}$ and $R^{13}$ are as described above.

In the unsaturated compound (1) to be used for producing the chromans of the present invention, $R^1$, $R^2$, $R^3$ and $R^4$ each independently represent a hydrogen atom, alkyl groups such as methyl group, ethyl group, n-propyl group, butyl group, 2-methylbutyl group, t-butyl group, n-pentyl group, 1-methylpentyl group, neopentyl group, 4-methylpentyl group, hexyl group, isohexyl group, heptyl group, octyl group, nonyl group, decyl group, 4, 8, 12-trimethyldecyl group, undecyl group, dodecyl group, tridecyl group, tetradecyl group, pentadecyl group, hexadecyl group, heptadecyl group, octadecyl group, nonadecyl group and eicosyl group; aryl groups such as phenyl group, naphthyl group, furyl group and thienyl group; the alkyl groups and aryl groups described above and further substituted with substituents such as alkyl group, aryl group, halogen atom, alkoxycarbonyl group, nitro group, cyano group, protected hydroxyl group and protected amino group. These substituents may be present on any of the other groups that may be substituted as described above.

In that case, as the protective groups in the protected hydroxyl group and protected amino group, for example, protective groups described in "Protective Groups in Organic Synthesis", 2nd edition, John Wiley & Sons (1991), pp. 10–142 and pp.309–405, incorporated herein by reference, may be used.

With not any limitation, specific examples of the unsaturated compound (1) include aliphatic unsaturated hydrocarbons such as 1-octene, 2,6-dimethyl-1-heptene, 2,6,10, 14-tetramethyl-1-pentadecene, and 2,6-dimethyl-1,5-heptadiene; unsaturated hydrocarbons with aromatic groups, such as styrene; hydrocarbons having a carbon-carbon double bond with an alkyl group and aryl group, substituted with nitro group and nitrophenyloxy group, such as 2-(4-nitrophenyloxy) methyl-1-propene.

In step 2 of the present invention, so as to give the desired chromans in a smooth manner in a high yield, the unsaturated compound (1) is used preferably within the range of 0.8 to 20 molar equivalents based on one molar equivalent of the alkoxymethylphenol compound, more preferably within the range of 1 to 10 molar equivalents to one molar equivalent of the alkoxymethylphenol compound.

Additionally, step 2 can be conducted without solvent or in the presence of solvent. When solvent is used, inert solvents such as decalin, mesitylene, and N-methylpyrrolidone may be used, and the amount of the solvent is preferably within the range of 50 to 500 parts by weight based on 100 parts by weight of the alkoxymethylphenol compound, inclusive of all specific values and subranges therebetween (e.g., 100, 200, 250, 300, 350, 400 and 450 parts by weight based on 100 parts by weight of the alkoxymethylphenol compound).

Step 2 for producing chromans is conducted by mixing together given amounts of the alkoxymethylphenol compound, the unsaturated compound (1) and the solvent if necessary, and heating the resulting mixture at a temperature of 150° C. or more (e.g., 155, 160, 165, 170, 175, 180, 185 and 200° C., or more). When the boiling point of the unsaturated compound to be used is lower than the aforementioned reaction temperature, the reaction is preferably promoted under pressurizing conditions. The reaction time may be varied, depending on the types of the alkoxymethylphenol compound and the unsaturated compound to be used, the ratio thereof to be used, and the reaction temperature, but generally, the reaction time is preferably adopted within the range of 30 minutes to 48 hours, inclusive of all specific values and subranges therebetween including 1, 2, 5, 10, 15, 20, 24, 30, 35, 40 and 45 hour reaction times.

The desired chromans can be produced in the present invention by sequentially conducting step 1 of producing the alkoxymethylphenol compound by reacting a phenol compound, a formaldehyde and an alcohol and step 2 of reacting the alkoxymethylphenol compound obtained at step 1 with the unsaturated compound (1), as described above.

However, the present invention is not limited to the process for producing chromans at such two-step reaction process, but the chromans may satisfactorily be produced by one-step process comprising reacting an alkoxymethylphenol compound with the ortho position to the phenolic hydroxyl group being substituted with an alkoxymethyl group as a starting material with the unsaturated compound (1) at a temperature of 150° C. or more, and thus, the present invention contains the process for producing chromans in such a one-step process.

The means for procuring the alkoxymethylphenol compound to be used as the starting material is not limited specifically, for example, such a compound which is preliminarily prepared separately or commercially available may satisfactorily be used. Additionally, the reaction of the alkoxymethylphenol compound with the unsaturated compound (1) may satisfactorily be conducted under the same conditions as those for step 2.

According to the process for producing chromans in such a one-step process, the alkoxymethylphenol compound represented by the general formula (3) as the alkoxymethylphenol compound as the starting material may preferably be used, and more preferably, the novel alkoxymethylphenol compound represented by the general formula (2) in the present invention, among the aforementioned compounds are used.

Unless noted otherwise, the hydrocarbon groups (e.g., alkyl, aryl or aralkyl) or hydrocarbon moieties of the groups described above may contain 1 to 30 carbon atoms, inclusive of all specific values and subranges therebetween (e.g., 2, 3, 4, 5, 6, 10, 12, 15, 20 and 25 carbon atoms).

The yield of the alkoxymethylphenol compound may be at least 25%, at least 35%, at least 50%, at least 65%, at least 75% at least 85%, at least 90%, at least 95%, and up to 100%, inclusive of all specific values and subranges therebetween, based on the starting phenol compound. The yield of the chroman may be at least 25%, at least 35%, at least 50%. at least 65%, at least 75%, at least 85%, at least 90%, at least 95%, and up to 100%, inclusive of all specific values and subranges therebetween, based on the alkoxymethylphenol compound.

EXAMPLES

The present invention will now be described in detail below, but it should however be borne in mind that the present invention is not limited to or by the following examples.

Example 1

Synthesis of 2,5,7,8-tetramethyl-6-acetoxy-2-(4-nitrophenyloxy)methylchroman (1) 4-Acetoxy-2,3,5-trimethylphenol (970 mg; 5.0 mmol), 80% paraformaldehyde (210 mg; 5.5 mmol), 1-butanol (2.43 g; 32.8 mmol), dibutylamine (65 mg; 0.5 mmol) and acetic acid (150 mg; 2.5 mmol) were mixed together, then the mixture was reacted at 100° C. with stirring for 7 hours. After completion of the reaction, toluene (10 ml) was added into the resulting mixture for extraction of the resulting product in toluene, and then the toluene phase was separated. After the separated toluene phase was sequentially washed with water, an aqueous 1% dilute sulfuric acid solution, an aqueous 5% sodium hydrogen carbonate solution and water, the toluene phase was distilled under reduced pressure to distill off compounds with low boiling points, to give 1.27 g of an oily product (yield: 95%). The $^1$H-NMR data of the oily product was shown below, and based on the data, it was confirmed that the oily product was 4-acetoxy-2,3,5-trimethyl-6-butoxymethyl-1-hydroxybenzene. δ ppm (CDCl$_3$, 300 MHz); 8.30 (1H, s), 4.73 (2H, s), 3.55 (2H, t, J=6.5 Hz), 2.32 (3H, s), 2.15 (3H, s) 2.04 (3H, s), 2.00 (3H, s), 1.62 (2H, m), 1.39 (2H, m), 0.93 (3H, t, J=7.4 Hz).

(2) Into the 4-acetoxy-2,3,5-trimethyl-6-b itoxymethyl-1-hydroxybenzene obtained above in (1) (1.27 g; 4.75 mmol) was added 2- (4-nitrophenyloxy)methyl-1-propene (2.9 g; 15 mmol), and the mixture was heated at 160° C. with stirring for 5 hours. After completion of the reaction, the reaction solution was analyzed by an internal standard method by liquid chromatography, which indicates that 2,5,7,8-tetramethyl-6-acetoxy-2-(4-nitrophenyloxy) methylchroman was generated at a yield of 60% (based on 4-acetoxy-2,3,5-trimethylphenol).

The $^1$H-NMR data of 2,5,7,8-tetramethyl-6-acetoxy-2-(4-nitrophenyloxy)methylchroman thus obtained was as shown below. δ ppm (CDCl$_3$, 300 MHz); 8.20 (2H, d, J=9 Hz), 6.97 (2H, d, J=9 Hz), 4.10 (1H, d, J=9 Hz), 3.98 (1H, d, J=9 Hz), 2.6(2H, broad, t, J=6 Hz), 2.31 (3H, s), 2.05 (3H, s), 2.02 (3H, s), 1.98 (3H, s), about 2 (2H, s).

Example 2

By carrying out a reaction in the same manner as in Example 1 (1) and (2), except for the use of 1-octanol (2.48 g; 19.1 mmol) instead of 1-butanol (2.43 g; 32.8 mmol), 2,5,7,8-tetramethyl-6-acetoxy-2-(4-nitrophenyloxy) methylchroman was generated at a yield of 58% (based on 4-acetoxy-2,3,5-trimethylphenol).

Example 3

By carrying out a reaction in the same manner as in Example 1 (1) and (2), except for the use of 2-propanol (2.36 g; 39.3 mmol) instead of 1-butanol (2.43 g; 32.8 mmol), 2,5,7,8-tetramethyl-6-acetoxy-2-(4-nitrophenyloxy) methylchroman was generated at a yield of 55% (based on 4-acetoxy-2,3,5-trimethylphenol).

Example 4

Synthesis of 2,6,8-trimethyl-2-(4-nitrophenyloxy) methylchroman (1) 2,4-Dimethylphenol (3.66 g; 30.0 mmol), 87.3% paraformaldehyde (1.24 g; 36.0 mmol), 1-butanol (14.46 g; 195.0 mmol), dibutylamine (0.39 g; 3.0 mmol) and acetic acid (0.90 g; 15.0 mmol) were mixed together, then the mixture was reacted under reflux with stirring for 11 hours. After completion of the reaction, toluene was added into the resulting mixture for extraction of the resulting product in toluene, and then the toluene phase was separated. After the separated toluene phase was sequentially washed with water, an aqueous 1% dilute sulfuric acid solution, an aqueous 5% sodium hydrogen carbonate solution and water, the toluene phase was distilled under reduced pressure to distill off compounds with low boiling points, to give 2,4-dimethyl-6-butoxymethyl-1-hydroxybenzene.

(2) Into the 2,4-dimethyl-6-butoxymethyl 1-hydroxybenzene obtained above in (1) was added 2-(4-nitrophenyloxy)methyl-1-propene (11.59 g; 60 mmol), and the mixture was heated at 160° C. with stirring for 25 hours. After completion of the reaction, the reaction solution was purified by silica gel column chromatography (hexane:ethyl acetate=15:1), to give 6.81 g of 2,6,8-trimethyl-2-(4-nitrophenyloxy)methylchroman (the yield based on 2,4-dimethylphenol: 69.4%).

The $^1$H-NMR data of 2,6,8-trimethyl-2-(4-nitrophenyloxy)methylchroman thus obtained was as shown below. δ ppm (CDCl$_3$, 300 MHz); 8.18 (2H, m), 7.00 (2H, m), 6.79 (1H, s), 6.72 (1H, s), 4.03 (2H, m), 2.76 (2H, m), 2.16 (8H, m), 1.44 (3H, s).

Example 5

Synthesis of Vitamin E Acetate (1) 4-Acetoxy-2, 3, 5-trimethylphenol (1.8 g; 9.3 mmol), 87.3 % paraformaldehyde (0.38 g; 11.2 mmol), 1-butanol (4.48 g; 60.5 mmol), dibutylamine (0.12 g; 0.93 mmol) and acetic acid (0.28 g; 4.7 mmol) were mixed together, then the mixture was reacted under reflux with stirring for 7 hours. After completion of the reaction, toluene was added into the resulting mixture for extraction of the resulting product in toluene, and then the toluene phase was separated. After the separated toluene phase was sequentially washed with water, an aqueous 1% dilute sulfuric acid solution, an aqueous 5% sodium hydrogen carbonate solution and water, the toluene phase was distilled under reduced pressure to distill off compounds with low boiling points, to give 4-acetoxy-2,3,5-trimethyl-6-butoxymethyl-1-hydroxybenzene.

(2) Into the 2,6,10,14-tetramethyl-1-pentadecene (13.7 g; purity of 91%; 47.0 mmol) was dropwise added a solution (11.7 g) of 4-acetoxy-2,3,5-trimethyl-6-butuxymethyl-1-hydroxybenzene obtained above in (1) in butanol under reduced pressure (260 mmHg) at 160° C., and then the resulting mixture was reacted at 160° C. with stirring for 18 hours. After completion of the reaction, the reaction solution was purified by silica gel column chromatography (hexane:ethyl acetate=25:1), to give 3.96 g of vitamin E acetate (yield based on 4-acetoxy-2,3,5-trimethylphenol: 90%).

The $^1$H-NMR data of vitamin E acetate thus obtained was as shown below. δ ppm (CDCl$_3$, 300 MHz); 2.58–2.64 (2H, m), 2.34 (3H, s), 2.11 (3H, s), 2.00 (3H, s), 1.71–1.88 (2H, m), 1.49–1.64 (3H, m), 1.22–1.48 (12H, m), 1.25 (3H, s) (6H, m), 0.85–0.90 (12H, m).

Example 6

Synthesis of 2,5,7,8-tetramethyl-6-acetoxy-2-(4-nitrophenyloxy)methylchroman (1) 4-Acetoxy-2,3,5-trimethylphenol (18.42 g; 100.0 mmol), 87.3% paraformaldehyde (4.13 g; 120.0 mmol), 1-butanol (48.18 g; 650.0 mmol), diethylamine (0.73 g; 10.0 mmol) and acetic acid (3.03 g; 2.5 mmol) were mixed together, then the mixture was reacted under reflux with stirring for 9.5 hours. After completion of the reaction, toluene was added into the resulting mixture for extraction of the resulting product in toluene, and then the toluene phase was separated. After the separated toluene phase was sequentially washed with water, an aqueous 1% dilute sulfuric acid solution, an aqueous 5% sodium hydrogen carbonate solution and water, the toluene phase was distilled under reduced pressure to distill off compounds with low boiling points, to give 4-acetoxy-2,3,5-trimethyl-6-butoxymethyl-1-hydroxybenzene.

(2) Into the 4-acetoxy-2,3,5-trimethyl-6-butoxymethyl-1-hydroxybenzene obtained above in (1) was added 2-(4-nitrophenyloxy)methyl-1-propene (38.64 g; 200 mmol), and the mixture was heated at 160° C. with stirring for 19 hours. After completion of the reaction, the reaction solution was analyzed by an internal standard method by liquid chromatography, which indicates that 2,5,7,8-tetramethyl-6-acetoxy-2-(4-nitrophenyloxy)methylchroman was generated at a yield of 58% (based on 4-acetoxy-2,3,5-trimethylphenol).

Example 7

By carrying out a reaction in the same manner as in Example 6 (1) and (2), except for the use of dioctylamine (2.41 g; 10.0 mmol) instead of diethylamine (0.73 g; 10.0 mmol), 2,5,7,8-tetramethyl-6-acetoxy-2-(4-nitrophenyloxy)methylchroman was generated at a yield of 52% (based on 4-acetoxy-2,3,5-trimethylphenol).

Example 8

Synthesis of 2,5,7,8-tetramethyl-6-acetoxy-2-(4-nitrophenyloxy)methylchroman (1) 4-Acetoxy-2,3,5-trimethylphenol (5.83 g; 30.0 mmol), 87.3% paraformaldehyde (1.24 g; 36.0 mmol), 1-butanol (14.46 g; 195.0 mmol), dibutylamine (0.39 g; 3.0 mmol) and benzoic acid (1.83 g; 15.0 mmol) were mixed together, then the mixture was reacted under reflux with stirring for 6 hours. After completion of the reaction, toluene was added into the resulting mixture for extraction of the resulting product in toluene, and then the toluene phase was separated. After the separated toluene phase was sequentially washed with water, an aqueous 1% dilute sulfuric acid solution, an aqueous 5% sodium hydrogen carbonate solution and water, the toluene phase was distilled under reduced pressure to distill off compounds with low boiling points, to give 4-acetoxy-2,3,5-trimethyl-6-butoxymethyl-1-hydroxybenzene.

(2) Into the 4-acetoxy-2,3,5-trimethyl-6-butoxymethyl-1-hydroxybenzene obtained above in (1) was added 2-(4-nitrophenyloxy)methyl-1-propene (11.59 g; 60.0 mmol), and the mixture was heated at 160° C. with stirring for 8 hours. After completion of the reaction, the reaction solution was analyzed by an internal standard method by liquid chromatography, which indicates that 2,5,7,8-tetramethyl-6-acetoxy-2-(4-nitrophenyloxy)methylchroman was generated at a yield of 54% (based on 4-acetoxy-2,3,5-trimethylphenol).

Example 9

By carrying out a reaction in the same manner as in Example 8 (1) and (2), except for the use of n-octanoic acid (2.16 g; 15.0 mmol) instead of benzoic acid (1.83 g; 15.0 mmol), 2,5,7,8-tetramethyl-6-acetoxy-2-(4-nitrophenyloxy) methylchroman was generated at a yield of 50% (based on 4-acetoxy-2,3,5-trimethylphenol).

Reference Example 1

According to the process of U.S. Pat. No. 5,495,026, 2,5,7,8-tetramethyl-6-acetoxy-2-(4-nitrophenyloxy) methylchroman was synthesized. Specifically, 4-acetoxy-2,3,5-trimethylphenol (970 mg; 5.0 mmol), 80% paraformaldehyde (210 mg; 5.5 mmol), 2-(4-nitrophenyloxy) methyl-1-propene (2.9 g; 15 mmol), dibutylamine (65 mg; 0. 5 mmol) and acetic acid (150 mg; 2.5 mmol) were mixed together, and the mixture was reacted at 150 ° C. with stirring for 3 hours. After the completion of the reaction, the reaction solution was analyzed by an internal standard method by liquid chromatography, which indicates that 2,5,7,8-tetramethyl-6-acetoxy-2-(4-nitrophenyloxy) methylchroman was generated at a yield of 27% (based on 4-acetoxy-2,3,5-trimethylphenol).

Obviously, numerous modifications and variations of the present invention are possible in light of the above teachings. It is therefore to be understood that within the scope of the appended claims, the invention may be practiced otherwise than as specifically described herein.

Japanese Patent Application 9-207362, filed Jul. 17, 1997, is incorporated herein by reference in its entirety.

What is claimed is:

1. An alkoxymethylphenol compound represented by formula (2):

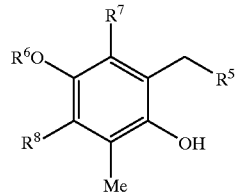

(2)

wherein
$R^5$ represents an alkoxyl group;
$R^6$ represents an aliphatic acyl group, an aromatic acyl group, benzyl group or a hydrogen atom; and
$R^7$ and $R^8$ each, independently, represent a hydrogen atom or a methyl group.

* * * * *